(12) United States Patent
Farrand et al.

(10) Patent No.: US 6,800,763 B2
(45) Date of Patent: Oct. 5, 2004

(54) REACTIVE THIENOTHIOPHENES

(75) Inventors: Louise Farrand, Spetisbury (GB); Marcus Thompson, Fordingbridge (GB); Mark Giles, Southampton (GB); Mark Goulding, Ringwood (GB); Martin Heeney, Southampton (GB); Steven Tierney, Southampton (GB); Maxim Shkunov, Southampton (GB); David Sparrowe, Bournemouth (GB); Iain McCulloch, Kings Somborne (GB)

(73) Assignee: Merck Patent Geselleshaft MIT Beschraenkter Haftung, Darmstadt (DE)

(*) Notice: Subject to any disclaimer, the term of this patent is extended or adjusted under 35 U.S.C. 154(b) by 0 days.

(21) Appl. No.: 10/190,512

(22) Filed: Jul. 9, 2002

(65) Prior Publication Data
US 2003/0080322 A1 May 1, 2003

(30) Foreign Application Priority Data
Sep. 7, 2001 (EP) .............................. 01115741

(51) Int. Cl.$^7$ .................. C07D 495/02; H01B 1/12; C09K 19/34; G02B 6/00; G02F 1/00

(52) U.S. Cl. .................. 549/50; 252/500; 528/377; 106/31.92; 385/141; 359/321

(58) Field of Search ............................ 549/50; 252/500; 528/377; 106/31.92; 359/321; 385/141

(56) References Cited

U.S. PATENT DOCUMENTS 6,403,809 B1 * 6/2002 Holmes et al.
6,515,144 B2 * 2/2003 Rajca
6,645,401 B2 * 11/2003 Giles et al.

* cited by examiner

*Primary Examiner*—Deborah C. Lambkin
(74) *Attorney, Agent, or Firm*—Millen White Zelano & Branigan, P.C.

(57) ABSTRACT

The invention relates to reactive thienothiophenes, their use as semiconductors or charge transport materials, in optical, electrooptical or electronic devices like for example organic field effect transistors (FET or OFET) for thin film transistor liquid crystal displays and integrated circuit devices such as RFID tags, electroluminescent devices in flat panel displays, and in photovoltaic and sensor devices, and to a field effect transistor, light emitting device or ID tag comprising the reactive thienothiophenes.

24 Claims, No Drawings

REACTIVE THIENOTHIOPHENES

FIELD OF INVENTION

The invention relates to reactive thienothiophenes. The invention further relates to their use as semiconductors or charge transport materials, in optical, electrooptical or electronic devices like for example organic field effect transistors (FET or OFET) for thin film transistor liquid crystal displays and integrated circuit devices such as radio frequency identification (RFID) tags, electroluminescent devices in flat panel displays, and in photovoltaic and sensor devices. The invention further relates to a field effect transistor, light emitting device or identification (ID) tag comprising the reactive thienothiophenes.

BACKGROUND AND PRIOR ART

Organic materials have recently shown promise as the active layer in organic based thin film transistors and organic field effect transistors [see H. E. Katz, Z. Bao and S. L. Gilat, Acc. Chem. Res., 2001, 34, 5, 359]. Such devices have potential applications in smart cards, security tags and the switching element in flat panel displays. Organic materials are envisaged to have substantial cost advantages over their silicon analogues if they can be deposited from solution, as this enables a fast, large-area fabrication route.

The performance of the device is principally based upon the charge carrier mobility of the semiconducting material and the current on/off ratio, so the ideal semiconductor should have a low conductivity in the off state, combined with a high charge carrier mobility ($>1 \times 10^{-3}$ cm$^2$ V$^{-1}$ s$^{-1}$). In addition, it is important that the semiconducting material is relatively stable to oxidation i.e. it has a high ionization potential, as oxidation leads to reduced device performance.

Compounds known in priort art for use as semiconductors are dithienothiophene (DTT) and its fused dimer α,α'-bis(dithieno[3,2-b:2',3'-d]thiophene (BDT) having the structures shown below.

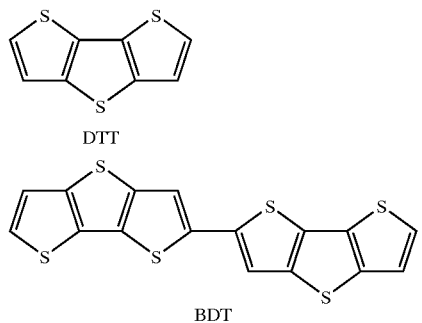

BDT and DDT are described for example in F. de Jong and M. J. Janssen, J. Org. Chem., 1971, 36, 12, 1645; S. Inaoka and D. M. Collard, J. Mater. Chem., 1999, 9, 1719; H. Sirringhaus et al, Appl. Phys. Lett. 1997, 71 (26), 3871; X-C. Li et al, J. Am. Chem. Soc., 1998, 120, 2206, and in the international patent application WO 99/12989.

In particular BDT, which has been extensively studied, has been shown to be an effective p-type semiconductor for organic FETs with a very high charge carrier mobility of 0.02–0.05 cm$^2$/V. BDT also has been found in the solid state to have a completely coplanar formation, and to be more planar than oligomers of thiophene.

However, the materials described in prior art have several disadvantages. BDT has a high melting point and is very insoluble, therefore, if used as the active layer in an organic thin film transistor, it cannot be readily solution processed.

As a result, for applications like FETs, prior art materials like DTT or BDT are usually deposited as a thin film by vacuum deposition, which is an expensive processing technique that is unsuitable for the fabrication of large-area films.

It was an aim of the present invention to provide new organic materials for use as semiconductors or charge transport materials, which are easy to synthesize, have high charge mobility, good processibility. The materials should be easily processible to form thin and large-area films for use in semiconductor devices. Other aims of the invention are immediately evident to those skilled in the art from the following description.

It was found that these aims can be achieved by providing reactive thienothiophenes as described below.

Definition of Terms

The terms 'liquid crystalline or mesogenic material' or 'liquid crystalline or mesogenic compound' means materials or compounds comprising one or more rod-shaped, lath-shaped or disk-shaped mesogenic groups, i.e. groups with the ability to induce liquid crystal phase behavior. The compounds or materials comprising mesogenic groups do not necessarily have to exhibit a liquid crystal phase themselves. It is also possible that they show liquid crystal phase behavior only in mixtures with other compounds, or when the mesogenic compounds or materials, or the mixtures thereof, are polymerized.

The term 'reactive group' or 'reactive compound' includes compounds or groups that are capable of participating in a polymerization reaction, like radicalic or ionic chain polymerization, polyaddition or polycondensation, as well as compounds or groups that are capable of being grafted for example by condensation or addition to a polymer backbone in a polymeranalogous reaction.

The term 'film' includes self-supporting, i.e. free-standing, films that show more or less pronounced mechanical stability and flexibility, as well as coatings or layers on a supporting substrate or between two substrates.

SUMMARY OF THE INVENTION

One object of the invention are compounds of formula I

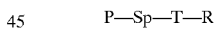

wherein
  P is a polymerizable or reactive group,
  Sp is a spacer group or a single bond,
  R is H, halogen, CN, NO$_2$, an aliphatic, alicyclic or aromatic group with up to 40 C atoms that may also comprise one or more hetero atoms and one or more fused rings, or P—Sp—, and
  T is a group comprising two or more fused thiophene rings.

Another object of the invention is the use of compounds of formula I as semiconductors or charge transport materials, in particular in optical, electrooptical or electronic devices, like for example components of integrated circuitry, field effect transistors (FET) for example as thin film transistors in flat panel display applications or for Radio Frequency Identification (RFID) tags, or in semiconducting components for organic light emitting diode (OLED) applications such as electroluminescent displays or backlights of flat panel displays, for photovoltaic or sensor devices, as electrode materials in batteries, as photoconductors and for electrophotographic applications.

Another object of the invention is a field effect transistor, for example as a component of integrated circuitry, as a thin film transistor in flat panel display applications, or in an RFID tag, comprising one or more compounds of formula I.

Another object of the invention is a semiconducting component, for example in OLED applications like electroluminescent displays or backlights of flat panel displays, in photovoltaic or sensor devices, as electrode materials in batteries, as photoconductors and for electrophotographic applications, comprising one or more compounds of formula I.

Another object of the invention is a security marking or device comprising an RFID or ID tag or a FET according to the invention.

DETAILED DESCRIPTION OF THE INVENTION

The compounds of formula I provide several advantages over prior art materials

- by adding substituent chains and other groups they can be made more soluble, thus being suitable for spin coating or solution coating techniques, rather than vacuum deposition, to prepare thin films for use e.g. in electronic devices such as transistors,
- they can be made mesogenic or liquid crystalline, thus exhibiting a higher degree of order that leads to particularly high charge carrier mobility, in particular when being aligned in their mesophase into macroscopically ordered orientation
- their macroscopic mesophase properties can be frozen in by in situ polymerization,
- they combine the properties of a semiconducting material with those of a mesogenic material to give novel materials with a rigid, planar conjugated core and a flexible chain to increase solubility and to decrease the melting point, which show high charge carrier mobility when being aligned in their mesophase.

The compounds of formula I are useful as charge transport semiconductors, in that they have high carrier mobilities. In particular, the introduction of alkyl side chains to the thienothiophene core improves the solubility and therefore the solution processibility of the compounds of formula I.

Particularly preferred are mesogenic or liquid crystalline compounds of formula I, wherein T is a mesogenic group. These compounds are particularly useful as semiconductors or charge transport materials, as they can be processed while in the highly ordered mesophase morphology, and readily aligned by conventional techniques in a preferred direction. Both smectic and nematic mesophase ordering allows close packing of molecular pi-electron systems, which maximizes intermolecular charge transfer which occurs through a hopping mechanism between adjacent molecules. This ordered, and oriented microstructure can be permanently "frozen-in" by polymerising the mesogens, which can also create a structure with long range order, or "monodomain". Formation of a monodomain also maximizes charge transfer by eliminating charge trap sites at grain boundaries, while the polymerization also improves the mechanical properies of the film. Further, by crosslinking the mesogens, a highly stable structure results, which has an additional advantage of being impervious to subsequent processing solvents during device fabrication, thus allowing a wider range of solvents to be used in deposition of the next layer of the device by solution techniques. In addition, it is often observed that this crosslinking further densities the film, leading to smaller intermolecular distances and improved charge transport.

It is also possible to copolymerize compounds of formula I via group P with other polymerizable mesogenic or liquid crystal monomers that are known from prior art, as well as with other compounds of formula 1, in order to induce or enhance liquid crystal phase behavior.

Thus, another object of the invention is a reactive liquid crystal mixture comprising one or more compounds of formula I and optionally comprising one or more further reactive compounds, wherein at least one of the compounds of formula I and/or the further reactive compounds is mesogenic or liquid crystalline.

Another object of the present invention is an anisotropic polymer film with charge transport properties obtainable from a reactive liquid crystal mixture as defined above that is aligned in its liquid crystal phase into macroscopically ordered orientation and polymerized or crosslinked to fix the oriented state.

Another object of the invention is a liquid crystal side chain polymer (SCLCP) obtained from a reactive liquid crystal material as defined above by polymerization or polymeranalogous reaction. Particularly preferred are SCLCPs obtained from one or more compounds according to formula I or from a reactive mixture comprising one or more compounds of formula I.

Another object of the invention is an SCLCP obtained from one or more compounds of formula I or from a reactive liquid crystal mixture as defined above, by copolymerization or polymeranalogous reaction together with one or more additional mesogenic or non-mesogenic comonomers.

Side chain liquid crystal polymers or copolymers (SCLCPs), in which the semiconducting component is located as a pendant group, separated from a flexible backbone by an aliphatic spacer group, offer the possibility to obtain a highly ordered lamellar like morphology. This structure consists of closely packed conjugated aromatic mesogens, in which very close (typically<4 Å) pi-pi stacking can occur. This stacking allows intermolecular charge transport to occur more easily, leading to high charge carrier mobilities. SCLCPs are advantageous for specific applications as they can be readily synthesized before processing and then e.g. be processed from solution in an organic solvent. If SCLCPs are used in solutions, they can orient spontaneously when coated onto an appropriate surface and when at their mesophase temperature, which can result in large area, highly ordered domains.

Particularly preferred are liquid crystal compounds of formula I, or liquid crystal mixtures comprising one or more compounds of formula I, that exhibit a nematic and/or smectic liquid crystal phase. For FET applications smectic materials are especially preferred. For OLED applications nematic or smectic materials are especially preferred. R in formula I is preferably H, F, Cl or straight chain, branched or cyclic alkyl with 1 to 20 C-atoms, which may be unsubstituted, mono- or poly-substituted by F, Cl, Br, I or CN, it being also possible for one or more non-adjacent $CH_2$ groups to be replaced, in each case independently from one another, by —O—, —S—, —NH—, —NR$^0$—, —SiR$^0$R$^{00}$—, —CO—, —COO—, —OCO—, —OCO—O—, —S—CO—, —CO—S—, —CH=CH— or —C≡C— in such a manner that O and/or S atoms are not linked directly to one another, or an aromatic or heteroaromatic group.

Particularly preferably R is optionally fluorinated alkyl or alkoxy with 1 to 15 C atoms.

Further preferred are compounds of formula I wherein R is P—Sp.

T in formula I is preferably a group comprising 2, 3, 4, 5 or 6 fused thiophene rings, in particular, preferably a group comprising 2–6 thiophene rings, wherein these rings are fused in 2, 3 and/or 4,5-position in linear fashion, it also being possible for groups of 2, 3, 4 or 5 fused thiophene rings to be connected via single bonds in 2- and/or 5-position to other single or fused thiophene rings, and wherein the thiopene rings may be substituted in 3- and/or 4-position by $R^1$ said group T comprising at least one subgroup with at least two fused thiophene rings.

Particularly preferably T is selected of formula II

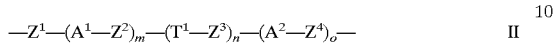

$$-Z^1-(A^1-Z^2)_m-(T^1-Z^3)_n-(A^2-Z^4)_o- \quad \text{II}$$

wherein $A^1$ and $A^2$ are independently of each other an aromatic, heteroaromatic, alicyclic or heterocyclic group with up to 18 C atoms which is unsubstituted, mono- or polysubstituted with $R^1$, and $A^1$ may also denote $T^1$, $Z^1$ to $Z^4$ are independently of each other —O—, —S—, —CO—, —COO—, —OCO—, —O—COO—, —CO—NR$^0$—, —NR$^0$—CO—, —OCH$_2$—, —CH$_2$O—, —SCH$_2$—, —CH$_2$S—, —CF$_2$O—, —OCF$_2$—, —CF$_2$S—, —SCF$_2$—, —CH$_2$CH$_2$—, —CF$_2$CH$_2$—, —CH$_2$CF$_2$—, —CF$_2$CF$_2$—, —CH=N—, —N=CH—, —N=N—, —CH=CR$^0$—, —CX$^1$=CX$^2$—, —C≡C—, —CH=CH—COO—, —OCO—CH=CH— or a single bond, $X^1$ and $X^2$ are independently of each other H, F, Cl or CN, $T^1$ is a group consisting of 2, 3, 4, 5 or 6 fused thiophene rings which may also be substituted by $R^1$, $R^1$ is H, halogen, CN, NO$_2$, straight chain, branched or cyclic alkyl with 1 to 20 C-atoms, which may be unsubstituted, mono- or poly-substituted by F, Cl, Br, I or CN, it being also possible for one or more non-adjacent CH$_2$ groups to be replaced, in each case independently from one another, by —O—, —S—, —NH—, —NR$^0$—, —SiR$^0$R$^{00}$—, —CO—, —COO—, —OCO—, —OCO—O—, —S—CO—, —CO—S—, —CH=CH— or —C≡C— in such a manner that O and/or S atoms are not linked directly to one another, an aromatic or heteroaromatic group, or P—Sp, $R^0$ and $R^{00}$ are independently of each other H or alkyl with 1 to 12 C-atoms, m and o are independently of each other 0, 1, 2 or 3, and n is 1, 2 or 3.

Particularly preferred groups T are those wherein $Z^1$, $A^1$, $Z^2$, $T^1$, $Z^3$, $A^2$ and $Z^4$ form a conjugated pi-system. Therein $A^1$ and $A^2$ are preferably arylene or heteroarylene and $Z^1$, $Z^2$, $Z^3$ and $Z^4$ are preferably a single bond or a conjugated link such as —CX$^1$=CX$^2$— or —C≡C—.

Further preferred groups T are those wherein m and o are 0, further those wherein m and o are 1 or 2.

Further preferred groups T are those wherein $T^1$ is dithienothiophene that may also be substituted with $R^1$ as defined above, furthermore those wherein n is 1 or 2 and $Z^2$ is a single bond or a conjugated link such as —CX$^1$=CX$^2$— or —C≡C—.

Particularly preferred groups T are those of the following formulae

| | |
|---|---|
| —Z$^1$—T$^1$—Z$^3$— | II1 |
| —Z$^1$—A$^1$—Z$^2$—T$^1$—Z$^3$— | II2 |
| —Z$^1$—T$^1$—Z$^3$—T$^1$—Z$^3$— | II3 |
| —Z$^1$—A$^1$—Z$^2$—T$^1$—Z$^3$—A$^2$—Z$^4$— | II4 |
| —Z$^1$—A$^1$—Z$^2$—A$^1$—Z$^2$—T$^1$—Z$^3$— | II5 |
| —Z$^1$—A$^1$—Z$^2$—T$^1$—Z$^3$—T$^1$—Z$^3$— | II6 |
| —Z$^1$—T$^1$—Z$^2$—A$^1$—Z$^2$—T$^1$—Z$^3$— | II7 |
| —Z$^1$—A$^1$—Z$^2$—A$^1$—Z$^2$—T$^1$—Z$^3$—A$^2$—Z$^4$— | II8 |
| —Z$^1$—A$^1$—Z$^2$—A$^1$—Z$^2$—A$^1$—Z$^2$—T$^2$—Z$^3$— | II9 |
| —Z$^1$—A$^1$—Z$^2$—A$^1$—Z$^2$—T$^1$—Z$^3$—T$^2$—Z$^3$— | II10 |
| —Z$^1$—A$^1$—Z$^2$—T$^1$—Z$^2$—A$^1$—Z$^2$—T$^2$—Z$^3$— | II11 |
| —Z$^1$—A$^1$—Z$^2$—T$^1$—Z$^3$—T$^1$—Z$^3$—A$^2$—Z$^4$— | II12 |
| —Z$^1$—T$^1$—Z$^2$—A$^1$—Z$^2$—A$^1$—Z$^2$—T$^2$—Z$^3$— | II13 |
| —Z$^1$—A$^1$—Z$^2$—T$^1$—Z$^3$—T$^1$—Z$^3$—T$^1$—Z$^3$— | II14 |
| —Z$^1$—T$^1$—Z$^2$—A$^1$—Z$^2$—T$^1$—Z$^3$—T$^1$—Z$^3$— | II15 |
| —Z$^1$—A$^1$—Z$^2$—A$^1$—Z$^2$—A$^1$—Z$^2$—A$^1$—Z$^2$—T$^1$—Z$^3$— | II16 |
| —Z$^1$—A$^1$—Z$^2$—A$^1$—Z$^2$—A$^1$—Z$^2$—T$^1$—Z$^3$—A$^1$—Z$^4$— | II17 |
| —Z$^1$—A$^1$—Z$^2$—A$^1$—Z$^2$—T$^1$—Z$^3$—A$^2$—Z$^4$—A$^2$—Z$^4$— | II18 |
| —Z$^1$—A$^1$—Z$^2$—A$^1$—Z$^2$—A$^1$—Z$^2$—T$^1$—Z$^3$—T$^1$—Z$^3$— | II19 |
| —Z$^1$—A$^1$—Z$^2$—A$^1$—Z$^2$—A$^1$—Z$^2$—A$^1$—Z$^2$—T$^1$—Z$^3$— | II20 |
| —Z$^1$—A$^1$—Z$^2$—T$^1$—Z$^2$—A$^1$—Z$^2$—A$^1$—Z$^2$—T$^1$—Z$^3$— | II21 |
| —Z$^1$—A$^1$—Z$^2$—A$^1$—Z$^2$—T$^1$—Z$^3$—T$^1$—Z$^3$—A$^2$—Z$^4$— | II22 |
| —Z$^1$—A$^1$—Z$^2$—T$^1$—Z$^2$—A$^1$—Z$^2$—T$^1$—Z$^3$—A$^2$—Z$^4$— | II23 |
| —Z$^1$—T$^1$—Z$^2$—A$^1$—Z$^2$—A$^1$—Z$^2$—A$^1$—Z$^2$—T$^1$—Z$^3$— | II24 |
| —Z$^1$—A$^1$—Z$^2$—A$^1$—Z$^2$—T$^1$—Z$^3$—T$^1$—Z$^3$—T$^1$—Z$^3$— | II25 |
| —Z$^1$—A$^1$—Z$^2$—T$^1$—Z$^2$—A$^1$—Z$^2$—T$^1$—Z$^3$—T$^1$—Z$^3$— | II26 |
| —Z$^1$—A$^1$—Z$^2$—T$^1$—Z$^2$—T$^1$—Z$^2$—A$^1$—Z$^2$—T$^1$—Z$^3$— | II27 |
| —Z$^1$—A$^1$—Z$^2$—T$^1$—Z$^3$—T$^1$—Z$^3$—T$^1$—Z$^3$—A$^2$—Z$^4$— | II28 |
| —Z$^1$—T$^1$—Z$^2$—A$^1$—Z$^2$—T$^1$—Z$^2$—A$^1$—Z$^2$—T$^1$—Z$^3$— | II29 |
| —Z$^1$—T$^1$—Z$^2$—A$^1$—Z$^2$—A$^1$—Z$^2$—T$^1$—Z$^3$—T$^1$—Z$^3$— | II30 | wherein $Z^1$, $Z^2$, $Z^3$, $Z^4$, $A^1$, $A^2$ and $T^1$ have in each case independently one of the meanings of formula II.

$T^1$ is preferably selected from the following subformulae

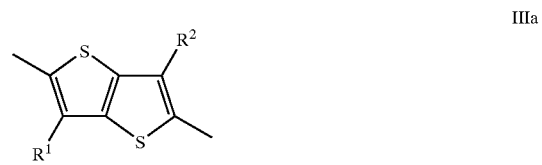

IIIa

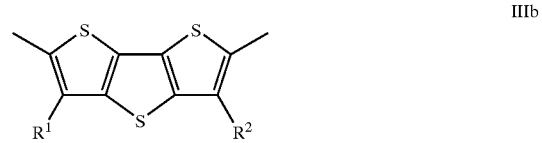

IIIb

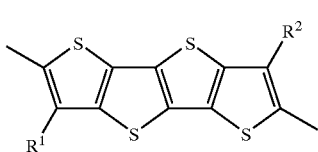
IIIc

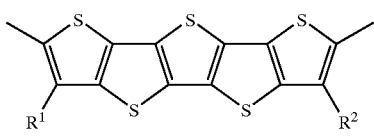
IIId

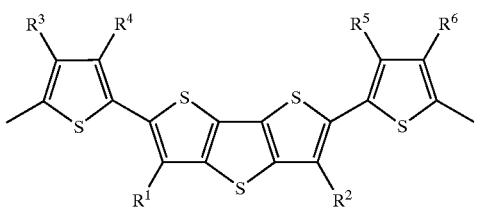
IIIe wherein $R^1$ has the meaning of formula II, and $R^2$, $R^3$, $R^4$, $R^5$ and $R^6$ have independently of each other one of the meanings of $R^1$ in formula II.

$A^1$ and $A^2$ are preferably selected from 1,4-phenylene, 1,4-cyclohexa-1,3-diene, 1,4-cyclohexenylene, in which, in addition, one or more CH groups may be replaced by N one or two non-adjacent $CH_2$ groups may be replaced by O and/or S, thiophene-2,5-diyl, thienothieophene-2,5-diyl, dithienothiophene-2,6-diyl, furan-2,5-diyl, 1,4-bicyclo-(2,2,2)-octylene, naphthalene-2,6-diyl, and indane-2,5-diyl, it being possible for all of these groups to be unsubstituted, mono- or polysubstituted by L, with L being halogen, CN, SCN, $NO_2$, $SF_5$ or an alkyl, alkoxy, alkylcarbonyl or alkoxycarbonyl group with 1 to 4 C atoms, wherein one or more H atoms may be substituted with F or Cl.

$A^1$ and $A^2$ are particularly preferably 1,4-phenylene that is substituted with 1, 2 or 3 groups L as defined above, or thiophene-2,5-diyl, thienothieophene-2,5-diyl or 2,2' dithienothiophene all of which are optionally substituted with one or more groups L as defined above.

$Z^{1-4}$ are preferably selected from —O—, —S—, —OCH$_2$—, —CH$_2$O—, —SCH$_2$—, —CH$_2$S—, —CF$_2$O—, —OCF$_2$—, —CF$_2$S—, —SCF$_2$—, —CH$_2$CH$_2$—, —CF$_2$CH$_2$—, —CH$_2$CF$_2$—, —CF$_2$CF$_2$—, —CH=N—, —N=CH—, —N=N—, —CH=CR$^0$—, —CX$^1$=CX$^2$—, —C≡C— and a single bond, in particular from —CH=N—, —N=CH—, —N=N—, —CH=CR$^0$—, —CX$^1$=CX$^2$—, —C≡C— and a single bond.

In the foregoing and the following, arylene and heteroarylene preferably denote a bivalent mono-, bi- or tricyclic aromatic or heteroaromatic group with up to 15 C atoms that may also comprise condensed rings and is optionally substituted with one or more groups $R^1$. Very preferred arylene and heteroarylene groups are those having one of the preferred meanings of $A^1$ as given above and below.

—CX$^1$=CX$^2$— is preferably —CH=CH—, —CH=CF—, —CF=CH—, —CF=CF—, —CH=C(CN)— or —C(CN)=CH—.

In the formulae shown above, $R^1$ to $R^6$ are preferably selected from $C_1$–$C_{20}$-alkyl, $C_1$–$C_{20}$-fluoroalkyl, $C_1$–$C_{20}$-alkenyl, $C_1$–$C_{20}$-alkynyl, $C_1$–$C_{20}$-alkoxy, $C_1$–$C_{20}$-thioether, $C_1$–$C_{20}$-silyl, $C_1$–$C_{20}$-ester and $C_1$–$C_{20}$-amino.

If one of R or $R^1$ to $R^6$ is an alkyl or alkoxy radical, i.e. where the terminal $CH_2$ group is replaced by —O—, this may be straight-chain or branched. It is preferably straight-chain, has 2, 3, 4, 5, 6, 7 or 8 carbon atoms and accordingly is preferably ethyl, propyl, butyl, pentyl, hexyl, heptyl, octyl, ethoxy, propoxy, butoxy, pentoxy, hexoxy, heptoxy, or octoxy, furthermore methyl, nonyl, decyl, undecyl, dodecyl, tridecyl, tetradecyl, pentadecyl, nonoxy, decoxy, undecoxy, dodecoxy, tridecoxy or tetradecoxy, for example.

Oxaalkyl, i.e. where one $CH_2$ group is replaced by —O—, is preferably straight-chain 2-oxapropyl (=methoxymethyl), 2-(=ethoxymethyl) or 3-oxabutyl (=2-methoxyethyl), 2-, 3-, or 4-oxapentyl, 2-, 3-, 4-, or 5-oxahexyl, 2-, 3-, 4-, 5-, or 6-oxaheptyl, 2-, 3-, 4-, 5-, 6- or 7-oxaoctyl, 2-, 3-, 4-, 5-, 6-, 7- or 8-oxanonyl or 2-, 3-, 4-, 5-, 6-, 7-, 8- or 9-oxadecyl, for example.

Halogen is preferably F or Cl.

As used in P, "polymerizable group" is a standard term that is well known in the art, e.g., a group that can be polymerized via conventional polymerization process.

The polymerizable or reactive group P is preferably selected from $CH_2$=CW$^1$—COO—,

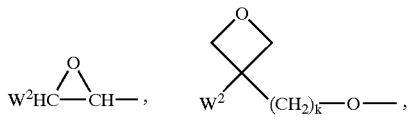

$CH_2$=CW$^2$—(O)$_{k1}$—, $CH_3$—CH=CH—O—, HO—CW$^2$W$^3$—, HS—CW$^2$W$^3$—, HW$^2$N—, HO—CW$^2$W$^3$—NH—, $CH_2$=CW$^1$—CO—NH—, $CH_2$=CH—(COO)$_{k1}$—Phe—(O)$_{k2}$—, Phe—CH=CH—, HOOC—, OCN— and W$^4$W$^5$W$^6$Si—, with W$^1$ being H, Cl, CN, phenyl or alkyl with 1 to 5 C-atoms, in particular H, $C_1$ or $CH_3$, W$^2$ and W$^3$ being independently of each other H or alkyl with 1 to 5 C-atoms, in particular methyl, ethyl or n-propyl, W$^4$, W$^5$ and W$^6$ being independently of each other Cl, oxaalkyl or oxacarbonylalkyl with 1 to 5 C-atoms, Phe being 1,4-phenylene and $k_1$ and $k_2$ being independently of each other 0 or 1.

Especially preferred groups P are $CH_2$=CH—COO—, $CH_2$=C(CH$_3$)—COO—, $CH_2$=CH—, $CH_2$=CH—O— and

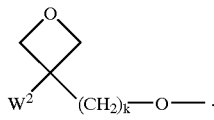

Very preferred are acrylate and oxetane groups. Oxetanes produce less shrinkage upon polymerization (cross-linking), which results in less stress development within films, leading to higher retention of ordering and fewer defects. Oxetane cross-linking also requires a cationic initiator, which unlike free radical initiators is inert to oxygen.

As for the spacer group Sp all groups can be used that are known for this purpose to the skilled in the art. The spacer group Sp is preferably of formula S-X, wherein S is alkylene with up to 20 C atoms which may be unsubstituted, mono- or poly-substituted by F, Cl, Br, I or CN, it being also possible for one or more non-adjacent $CH_2$ groups to be replaced, in each case independently from one another, by —O—, —S—, —NH—, —NR$^0$—, —SiR$^0$R$^{00}$—, —CO—, —COO—, —OCO—, —OCO—O—, —S—CO—, —CO—S—, —CH=CH— or —C≡C— in such a manner that O and/or S atoms are not linked directly to one another, X is —O—, —S—, —CO—, —COO—, —OCO—, —O—COO—, —CO—NR⁰—, —NR⁰—CO—, —OCH₂—, —CH₂O—, —SCH₂—, —CH₂S—, —CF₂O—, —OCF₂—, —CF₂S—, —SCF₂—, —CF₂CH₂—, —CH₂CF₂—, —CF₂CF₂—, —CH=N—, —N=CH—, —N=N—, —CH=CR⁰—, —CX¹=CX²—, —C≡C—, —CH=CH—COO—, —OCO—CH=CH— or a single bond, and R⁰ and R⁰⁰ have one of the meanings given above.

X is preferably —O—, —S—, —OCH₂—, —CH₂O—, —SCH₂—, —CH₂S—, —CF₂O—, —OCF₂—, —CF₂S—, —SCF₂—, —CH₂CH₂—, —CF₂CH₂—, —CH₂CF₂—, —CH=N—, —N=CH—, —N=N—, —CH=CR⁰—, —CX¹=CX²—, —C≡C— or a single bond, in particular —O—, —S—, —C≡C—, —CX¹=CX²— or a single bond, very preferably a group that is able to from a conjugated system, such as —C≡C— or —CX¹=CX²—, or a single bond.

In case the group P—S—X is linked to a group Z¹ or Z⁴, one of X and Z¹ or Z⁴ is preferably a single bond.

A spacer group is virtually any atom or group of atoms which distances P from T, and does not interfere the with polymerization reaction. Such spacer groups include, but are not limited to —(CH₂)ₚ—, —(SiR⁰R⁰⁰—O)ₚ—, —(CH₂CH₂O)ᵣ—CH₂CH₂—, —CH₂CH₂—S—CH₂CH₂— or —CH₂CH₂—NH—CH₂CH₂—, with p being an integer from 2 to 12, r being an integer from 1 to 3 and R⁰ and R⁰⁰ having the meanings given above.

Preferred spacer groups S are ethylene, propylene, butylene, pentylene, hexylene, heptylene, octylene, nonylene, decylene, undecylene, dodecylene, octadecylene, ethyleneoxyethylene, methyleneoxybutylene, ethylenethioethylene, ethylene-N-methyl-iminoethylene, 1-methylalkylene, ethenylene, propenylene and butenylene for example.

In case of compounds of formula I with more than one group P—Sp, the spacer groups Sp and/or the polymerizable groups P can be identical or different.

Further preferred are compounds with one or more groups P—Sp wherein Sp is a single bond.

SCLCPs obtained from the inventive compounds or mixtures by polymerization or copolymerization have a backbone that is formed by the polymerizable group P in formula I.

Particularly preferred are the following compounds

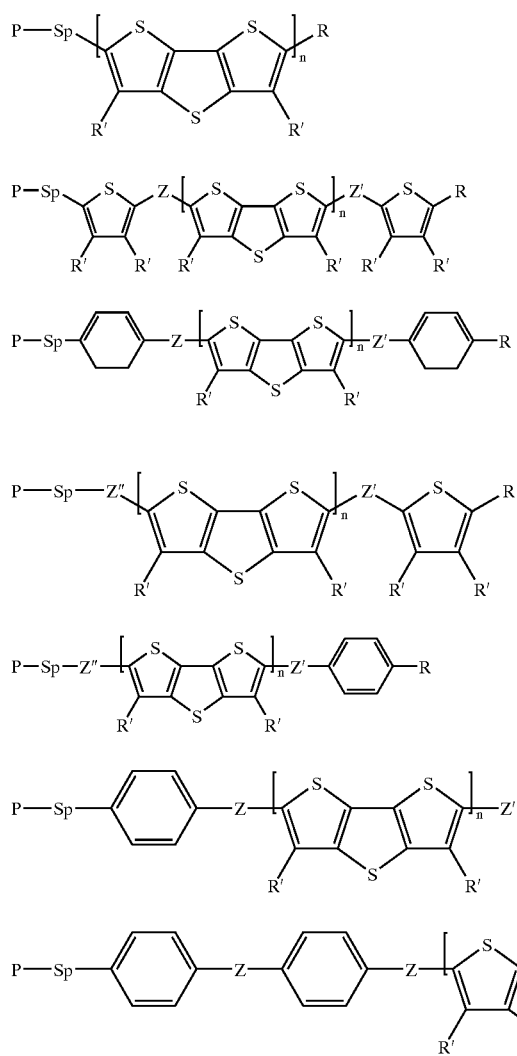

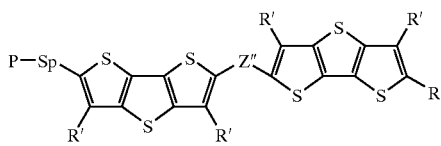 I13

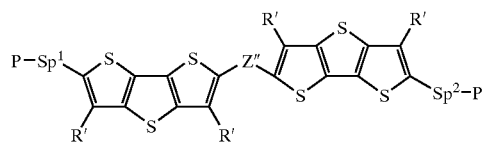 I14 wherein P, Sp and n have the meanings above,

Sp$^1$ and Sp$^2$ are different groups Sp as defined above,

Z and Z' have independently of each other one of the meanings of Z$^1$ in formula II, and are preferably —CH=CH—, —CH=CF—, —CF=CH—, CH=CCl—, —CCl=CH—, —CF=CF—, —CCl=CCl—, —C≡C— or a single bond, Z" has one of the meanings of Z$^1$ in formula II, and is preferably —CH=CH—, —CH=CF—, —CF=CH—, CH=CCl—, —CCl=CH—, —CF=CF—, —CCl=CCl— or —C≡C—, R has the meaning given above, and is preferably halogen, an optionally fluorinated alkyl groups with 1 to 15 C atoms or P—Sp—, R' has in each case independently one of the meanings of R$^1$ given above, and is preferably halogen, an optionally fluorinated alkyl group with 1 to 15 C atoms or P—Sp—.

The compounds of formula I can be synthesized according to or in analogy to methods that are known to the skilled in the art and are described for example in F. de Jong and M. J. Janssen, J. Org. Chem., 1971, 36, 12, 1645; S. Inaoka and D. M. Collard, J. Mater. Chem., 1999, 9, 1719 or WO 99/12989. Furthermore, they can be prepared according to or in analogy to the following reaction schemes. DTT and BTT can be prepared according to scheme 1.

Scheme 1

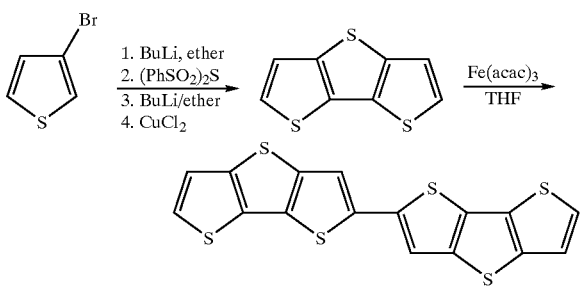

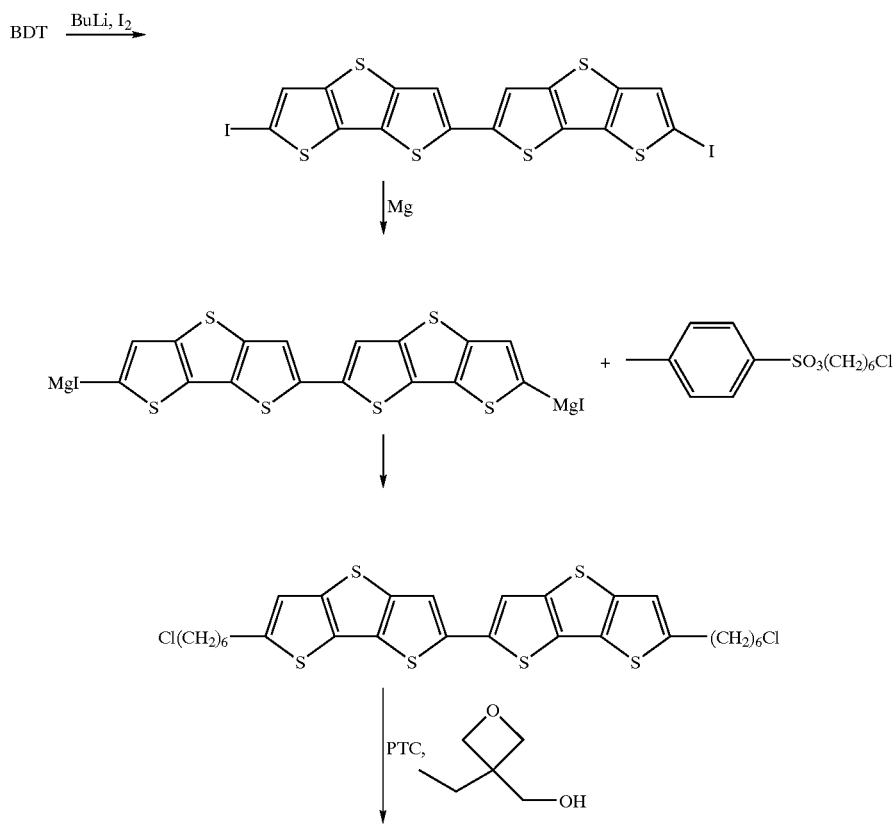

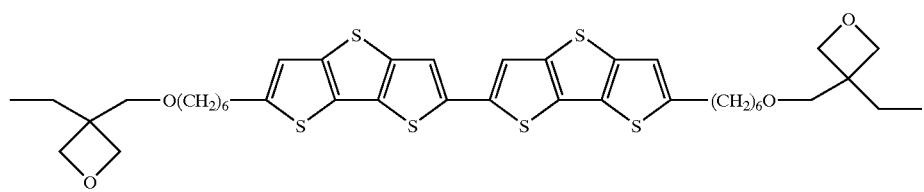
Scheme 3
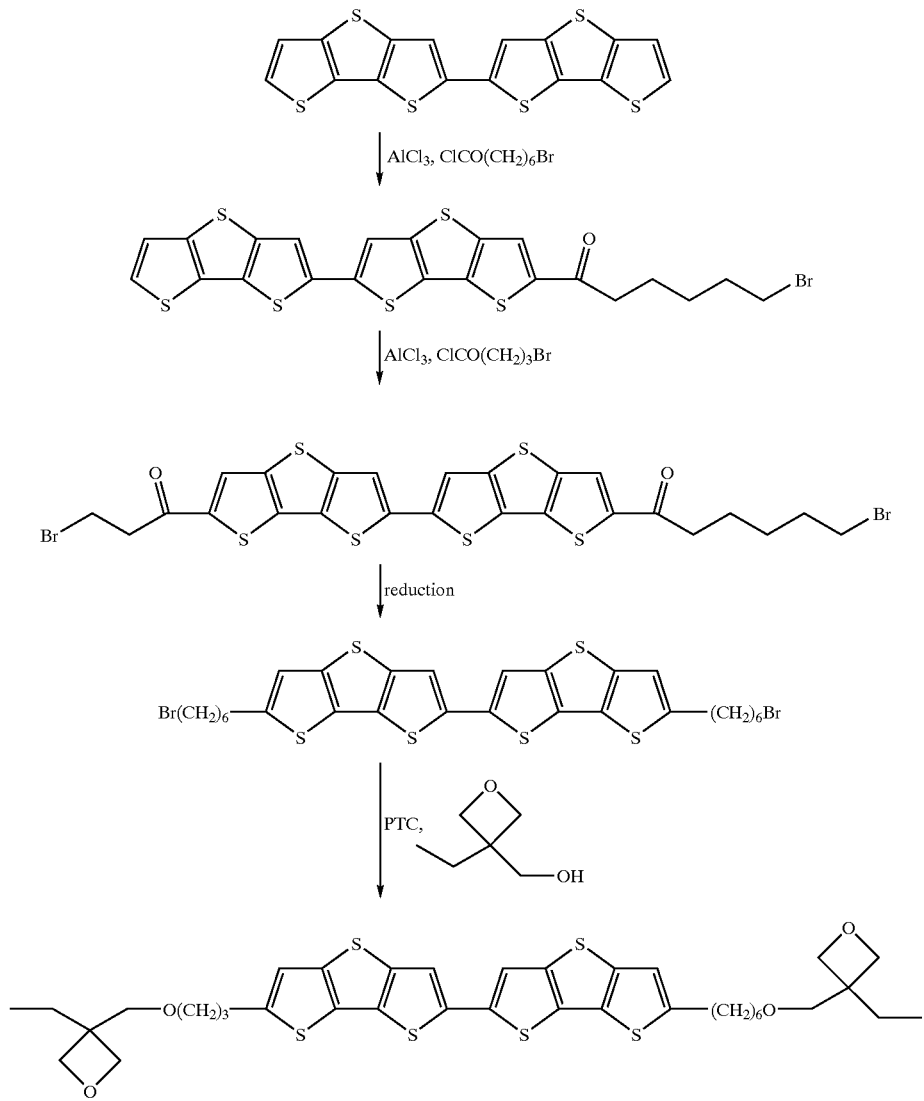
Scheme 4
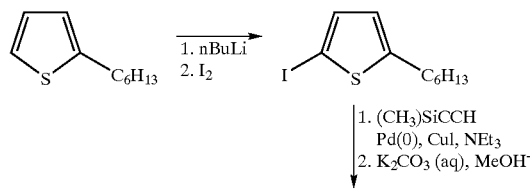

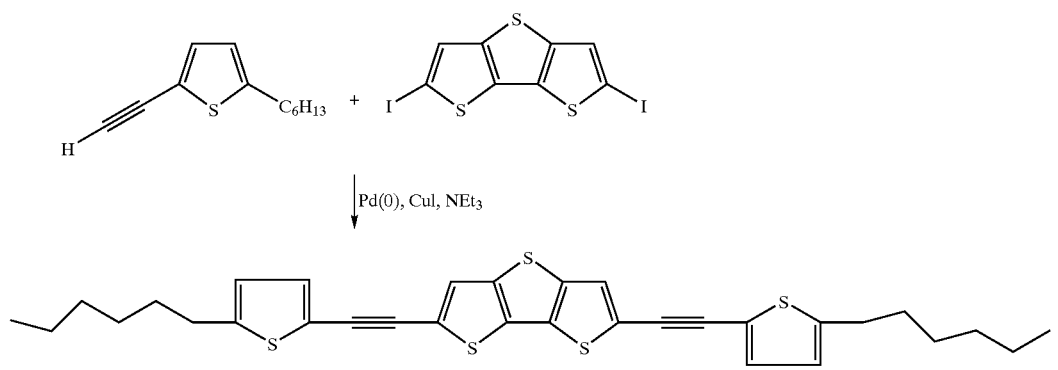
Scheme 5
DTT
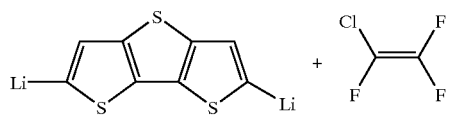
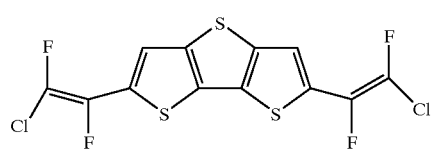
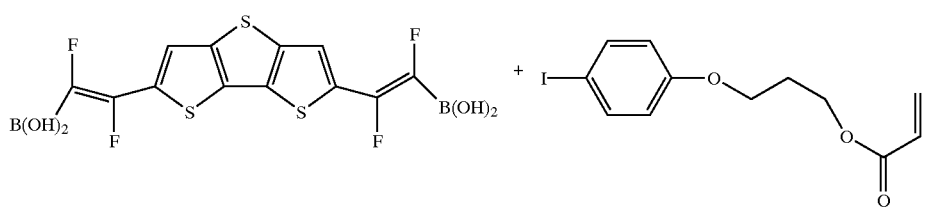
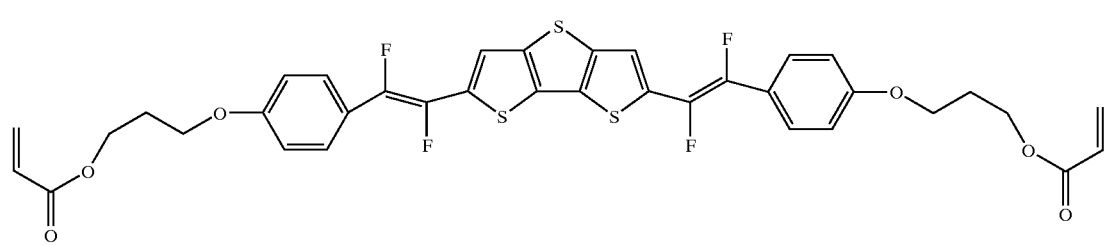

Scheme 6
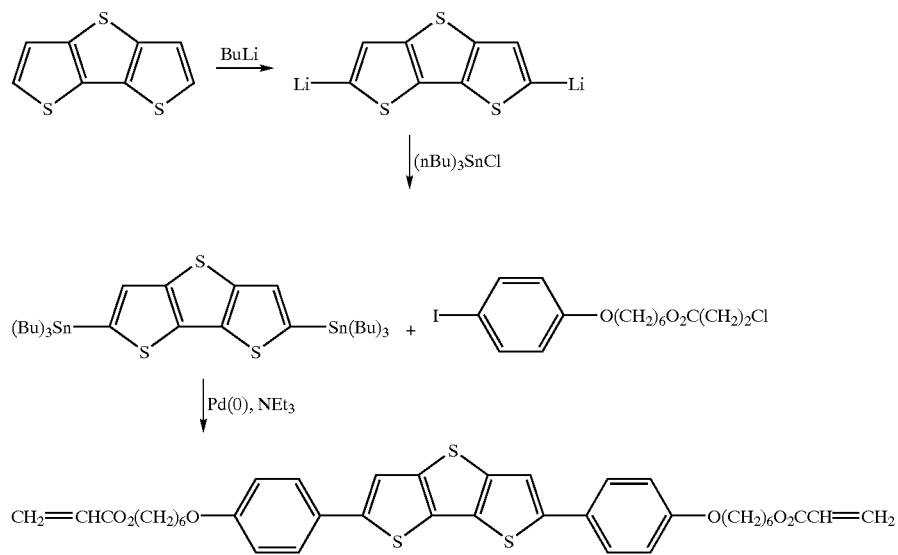
Scheme 7
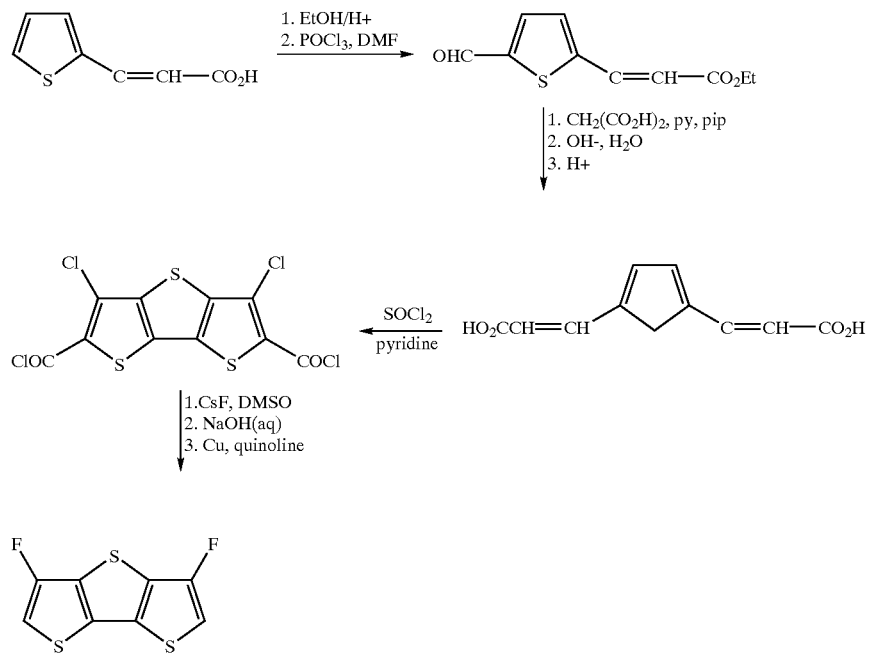
Scheme 8
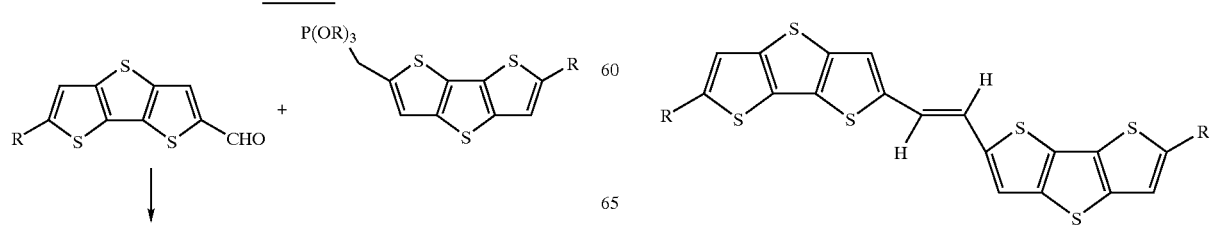

The novel synthesis methods and intermediates as disclosed in the above reaction schemes are another object of the present invention.

A further aspect of the invention relates to both the oxidized and reduced form of the compounds and materials according to this invention. Either loss or gain of electrons results in formation of a highly delocalized ionic form, which is of high conductivity. This can occur on exposure to common dopants. Suitable dopants and methods of doping are known to those skilled in the art, e.g. from EP 0 528 662, U.S. Pat. No. 5,198,153 or WO 96/21659.

The doping process typically implies treatment of the semiconductor material with an oxidating or reducing agent in a redox reaction to form delocalized ionic centers in the material, with the corresponding counterions derived from the applied dopants. Suitable doping methods comprise for example exposure to a doping vapor in the atmospheric pressure or at a reduced pressure, electrochemical doping in a solution containing a dopant, bringing a dopant into contact with the semiconductor material to be thermally diffused, and ion-implantantion of the dopant into the semiconductor material.

When electrons are used as carriers, suitable dopants are for example halogens (e.g. $I_2$, $Cl_2$, $Br_2$, ICl, $ICl_3$, IBr and IF), Lewis acids (e.g. $PF_5$, $AsF_5$, $SbF_5$, $BF_3$, $BCl_3$, $SbCl_5$, $BBr_3$ and $SO_3$), protonic acids, organic acids, or amino acids (e.g. HF, HCl, $HNO_3$, $H_2SO_4$, $HClO_4$, $FSO_3H$ and $ClSO_3H$), transition metal compounds (e.g. $FeCl_3$, FeOCl, $Fe(ClO_4)_3$, $Fe(4-CH_3C_6H_4SO_3)_3$, $TiCl_4$, $ZrCl_4$, $HfCl_4$, $NbF_5$, $NbCl_5$, $TaCl_5$, $MoF_5$, $MoCl_5$, $WF_5$, $WCl_6$, $UF_6$ and $LnCl_3$ (wherein Ln is a lanthanoid), anions (e.g. $Cl^-$, $Br^-$, $I^-$, $I_3^-$, $HSO_4^-$, $SO_4^{2-}$, $NO_3^-$, $ClO_4^{31}$, $BF_4^-$, $PF_6^-$, $AsF_6^-$, $SbF_6^-$, $FeCl_4^-$, $Fe(CN)_6^{3-}$, and anions of various sulfonic acids, such as aryl-$SO_3^-$). When holes are used as carriers, examples of dopants are cations (e.g. $H^+$, $Li^+$, $Na^+$, $K^+$, $Rb^+$ and $Cs^+$), alkali metals (e.g., Li, Na, K, Rb, and Cs), alkaline-earth metals (e.g., Ca, Sr, and Br), $O_2$, $XeOF_4$, $(NO_2^+)$ $(SbF_6^-)$, $(NO_2^+)$ $(SbCl_6^-)$, $(NO_2^+)$ $(BF_4^-)$, $AgClO_4$, $H_2IrCl_6$, $La(NO_3)_3$ $6H_2O$, $FSO_2OOSO_2F$, Eu, acetylcholine, $R_4N^+$, (R is an alkyl group), $R_4P^+$ (R is an alkyl group), $R_6As^+$ (R is an alkyl group), and $R_3S^+$ (R is an alkyl group).

The conducting form of the compounds and materials of the present invention can be used as an organic "metal" in applications, for example, but not limited to, charge injection layers and ITO planarizing layers in organic light emitting diode applications, films for flat panel displays and touch screens, antistatic films, printed conductive substrates, patterns ot tracts in electronic applications such as printed circuit boards and condensers.

The compounds of formula I can be polymerized, or copolymerized with other polymerizable compounds, via the polymerizable group P. This is preferably done by in-situ polymerization of a coated layer of the material, preferably during fabrication of the electronic or optical device comprising the compound of formula I. In case of liquid crystal materials, these are preferably aligned in their liquid crystal state into homeotropic orientation prior to polymerization, where the conjugated pi-electron systems are orthogonal to the direction of charge transport. This ensures that the intermolecular distances are minimised and hence then energy required to transport charge between molecules is minimized. The molecules are then polymerized or crosslinked to fix the uniform orientation of the liquid crystal state. Alignment and curing are carried out in the liquid crystal phase or mesophase of the material. This technique is known in the art and is generally described for example in D. J. Broer, et al., Angew. Makromol. Chem. 183, (1990), 45–66

Alignment of the liquid crystal material can be achieved for example by treatment of the substrate onto which the material is coated, by shearing the material during or after coating, by application of a magnetic or electric field to the coated material, or by the addition of surface-active compounds to the polymerizable material. Reviews of alignment techniques are given for example by I. Sage in "Thermotropic Liquid Crystals", edited by G. W. Gray, John Wiley & Sons, 1987, pages 75–77, and by T. Uchida and H. Seki in "Liquid Crystals—Applications and Uses Vol. 3", edited by B. Bahadur, World Scientific Publishing, Singapore 1992, pages 1–63. A review of alignment materials and techniques is given by J. Cognard, Mol. Cryst. Liq. Cryst. 78, Supplement 1 (1981), pages 1–77.

Polymerization takes place by exposure to heat or actinic radiation. Actinic radiation means irradiation with light, like UV light, IR light or visible light, irradiation with X-rays or gamma rays or irradiation with high energy particles, such as ions or electrons. Preferably polymerization is carried out by UV irradiation at a non-absorbing wavelength. As a source for actinic radiation for example a single UV lamp or a set of UV lamps can be used. When using a high lamp power the curing time can be reduced. Another possible source for actinic radiation is a laser, like e.g. a UV laser, an IR laser or a visible laser.

Polymerization is preferably carried out in the presence of an initiator absorbing at the wavelength of the actinic radiation. For example, when polymerising by means of UV light, a photoinitiator can be used that decomposes under UV irradiation to produce free radicals or ions that start the polymerization reaction. When curing polymerizable materials with acrylate or methacrylate groups, preferably a radical photoinitiator is used, when curing polymerizable materials with vinyl, epoxide and oxetane groups, preferably a cationic photoinitiator is used. It is also possible to use a polymerization initiator that decomposes when heated to produce free radicals or ions that start the polymerization. As a photoinitiator for radical polymerization for example the commercially available Irgacure 651, Irgacure 184, Darocure 1173 or Darocure 4205 (all from Ciba Geigy AG) can be used, whereas in case of cationic photopolymerization the commercially available UVI 6974 (Union Carbide) can be used.

The polymerizable material can additionally comprise one or more other suitable components such as, for example, catalysts, sensitizers, stabilizers, inhibitors, chain-transfer agents, co-reacting monomers, surface-active compounds, lubricating agents, wetting agents, dispersing agents, hydrophobing agents, adhesive agents, flow improvers, defoaming agents, deaerators, diluents, reactive diluents, auxiliaries, colourants, dyes or pigments.

The compounds of formula I can also be copolymerized with polymerizable mesogenic compounds to induce, or, in case of mesogenic materials of formula I, enhance liquid crystal phase behavior. Polymerizable mesogenic compounds that are suitable as comonomers are known in prior art and disclosed for example in WO 93/22397; EP 0,261, 712; DE 195,04,224; WO 95/22586 and WO 97/00600.

SCLCPs can be prepared from the polymerizable compounds or mixtures according to the invention by the methods described above, or by conventional polymerization techniques which are known to those skilled in the art, including for example radical, anionic or cationic chain polymerization, polyaddition or polycondensation. Polymerization can be carried out for example as polymerization in solution, without the need of coating and prior alignment, or polymerization in situ. It is also possible to form SCLCPs by grafting compounds according to the invention with a suitable reactive group, or mixtures thereof, to presynthesized isotropic or anisotropic polymer backbones in a polymer-analogous reaction. For example, compounds with a terminal hydroxy group can be attached to polymer backbones with lateral carboxylic acid or ester groups, compounds with terminal isocyanate groups can be added to backbones with free hydroxy groups, compounds with terminal vinyl or vinyloxy groups can be added e.g. to polysiloxane backbones with Si—H groups. It is also possible to form SCLCPs by copolymerization or polymeranalogous reaction from the inventive compounds together with conventional mesogenic or non mesogenic comonomers. Suitable comonomers are known to those skilled in the art. In principle it is possible to use all conventional comonomers known in the art that carry a reactive or polymerizable group capable of undergoing the desired polymer-forming reaction, like for example a polymerizable or reactive group P as defined above. Typical mesogenic comonomers are for example those mentioned in WO 93/22397; EP 0,261,712; DE 195, 04,224; WO 95/22586 and WO 97/00600. Typical non mesogenic comonomers are for example alkyl mono- or diacrylates or alkyl mono- or dimethacrylates with alkyl groups of 1 to 20 C atoms, like methyl acrylate or methyl methacrylate, trimethylpropane trimethacrylate or pentaerythritol tetraacrylate.

The compounds of formula I and the polymerizable mixtures and polymers obtained thereof are useful as optical, electronic and semiconductor materials, in particular as charge transport materials in field effect transistors (FETs) e.g. as components of integrated circuitry, ID tags or TFT applications. Alternatively, they may be used in organic light emitting diodes (OLEDs) in electroluminescent display applications or as backlight of e.g. liquid crystal displays, as photovoltaics or sensor materials, and for other semiconductor applications, as electrode materials in batteries, as photoconductors and for electrophotographic applications like electrophotographic recording.

Especially the oligomers and polymers according to the invention show advantageous solubility properties which allow production processes using solutions of these compounds. Thus films, including layers and coatings, may be generated by low cost production techniques e.g. spin coating. Suitable solvents or solvent mixtures comprise alkanes and/or aromatics, especially their fluorinated derivatives.

The materials of the present invention are useful as optical, electronic and semiconductor materials, in particular as charge transport materials in field effect transistors (FETs), as photovoltaics or sensor materials, for electrophotographic recording, and for other semiconductor applications. Such FETs, where an organic semiconductive material is arranged as a film between a gate-dielectric and a drain and a source electrode, are generally known e.g. from U.S. Pat. No. 5,892,244, WO 00/79617, U.S. Pat. No. 5,998,804, and from the references cited in the background and prior art chapter. Due to the advantages, like low cost production using the solubility properties of the compounds according to the invention and thus the processibility of large surfaces, preferred applications of these FETs are such as integrated circuitry, TFT-displays and security applications.

FETs comprising compounds of formula I or mixtures or polymers comprising them are suitable for example as ID tags in clothing, on food containers to register when food is out of date, on consumer products, household objects or any item which can be bought in a shop so that each item does not have to be priced individually, but for example many items can be passed through a reader at a register and all of the items in a shopping cart can be registered at the same time, saving manpower and time. In security applications they are suitable for use in field effect transistors for ID tags or security markings to authenticate and prevent counterfeiting of documents of value like banknotes, credit cards or ID cards, national ID documents, licenses or any product with money value, like stamps, tickets, shares, cheques etc.

Alternatively, the mono-, oligo- and polymers according to the invention may be used in organic light emitting devices or diodes (OLEDs), e.g. in display applications or as backlight of e.g. liquid crystal displays. Common OLEDs are realized using multilayer structures. An emission layer is generally sandwiched between one or more electron-transport and/or hole-transport layers. By applying an electric voltage electrons and holes as charge carriers move towards the emission layer where their recombination leads to the excitation and hence luminescence of the lumophor units contained in the emission layer. The inventive compounds, materials and films may be employed in one or more of the charge transport layers and/or in the emission layer, corresponding to their electrical and/or optical properties. Furthermore their use within the emission layer is especially advantageous, if the compounds, materials and films according to the invention show electroluminescent properties themselves or comprise electroluminescent groups or compounds. The selection, characterization as well as the processing of suitable monomeric, oligomeric and polymeric compounds or materials for the use in OLEDs is generally known by a person skilled in the art, see e.g. Meerholz, Synthetic Materials, 111–112, 2000, 31–34, Alcala, J. Appl. Phys., 88, 2000, 7124–7128 and the literature cited therein.

According to another use, the inventive compounds, materials or films, especially those which show photoluminescent properties, may be employed as materials of light sources, e.g. of display devices such as described in EP 0 889 350 A1 or by C. Weder et al., Science, 279, 1998, 835–837.

Furthermore, the compounds of the present invention are useful as high birefringence compounds added to liquid crystalline compositions in order to increase birefringence. For this purpose, they do not need to have a mesophase themselves, but a similar shape to conventional liquid crystals in order to dissolve and not to detract from the liquid crystal properties of the composition.

In the foregoing and in the following examples, unless otherwise indicated, all temperatures are set forth uncorrected in degrees Celsius and all parts and percentages are by weight. The following abbreviations are used to illustrate the liquid crystalline phase behavior of the compounds: K=crystalline; N=nematic; S=smectic; Ch=cholesteric; I=isotropic. The numbers between the symbols indicate the phase transition temperatures in ° C.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and, all parts and percentages are by weight, unless otherwise indicated.

The entire disclosure[s] of all applications, patents and publications, cited above or below, and of corresponding German application No. 01115741.9, filed Jul. 9, 2001, is hereby incorporated by reference.

EXAMPLE 1

Compound (3) was prepared as described below

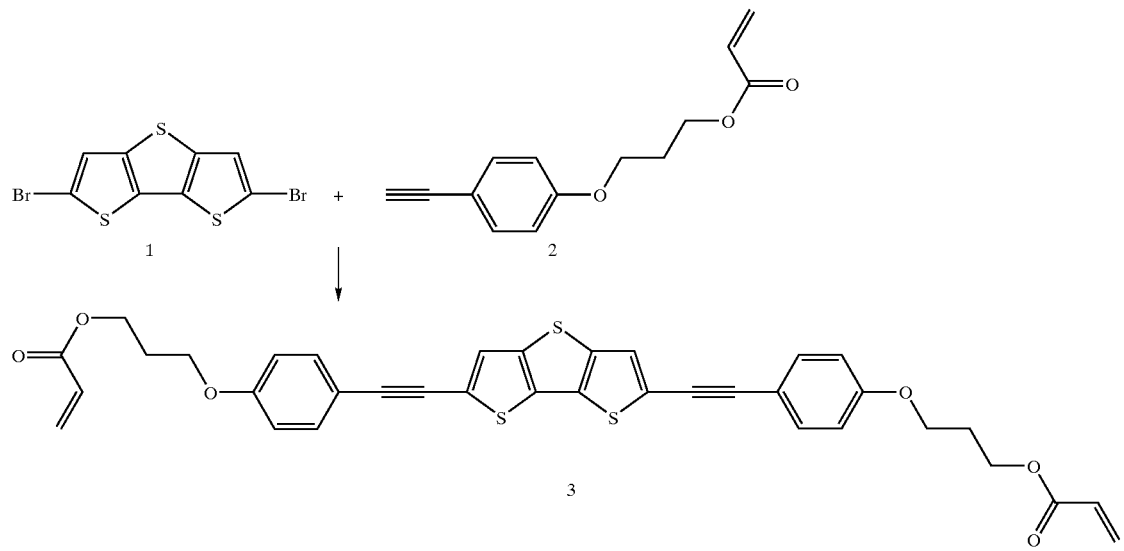

Acetylene compound (2) (1.34 g, 5.82 mmol) in THF was added dropwise to a solution of 2,2'dibromodithienothiophene (1) (0.68 g, 1.94 mmol), triethylamine (20 ml), Pd(PPh$_3$)$_2$Cl$_2$ (catalytic) and copper (1) iodide (catalytic) in THF (30 ml) under an atmosphere of nitrogen over a period of 2 hours at 40° C. After 16 h, the solution was allowed to cool to room temperature. The solution was poured in to dichloromethane and washed with water. The DCM layer was removed, dried over sodium sulphate and evaporated to dryness to leave a residual black solid. Purification was achieved by flash column chromatography using DCM:petrol (1:1). On evaporation of theappropriate fractions a yellow solid (0.5 g) was isolated.
$^1$H and $^{13}$C NMRs showed expected signals.

The following transitions and phases were observed by optical microscopy using crossed polarisers:
K-120-Sc-145-N-167-I

EXAMPLE 2

Compounds (5) and (6) were prepared as described below.

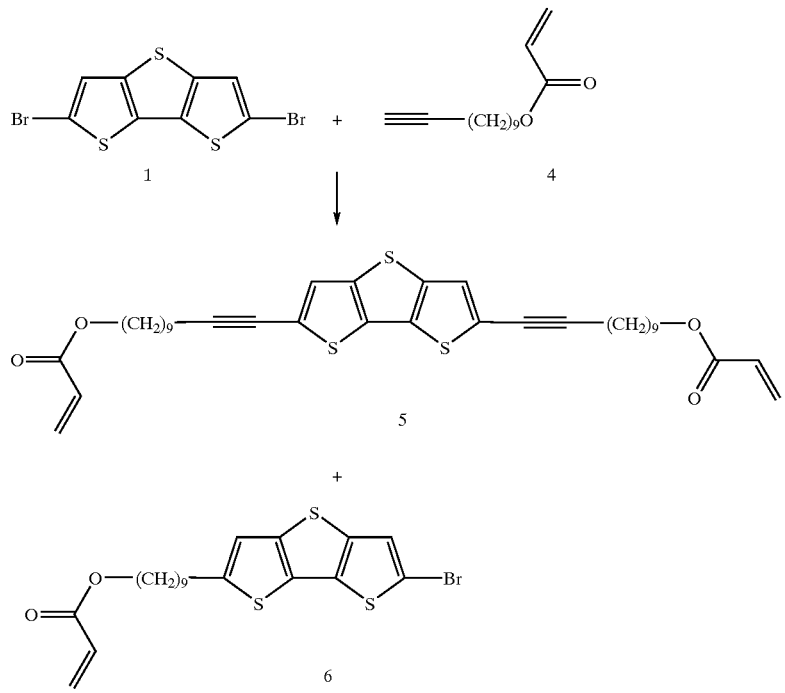

Acetylene compound (4) (6.58 g, 29.6 mmol) in THF was added dropwise to a solution of 2,2'dibromodithienothiophene (1) (10.2 g, 29.0 mmol), triethylamine (20 ml), Pd(PPh$_3$)$_2$Cl$_2$ (catalytic) and copper (1) iodide (catalytic) in THF (30 ml) under an atmosphere of nitrogen over a period of 2 hours at 40° C. After 16 h, the solution was allowed to cool to room temperature. The solution was poured in to dichloromethane and washed with water. The DCM layer was removed, dried over sodium sulphate and evaporated to dryness to leave a residual black solid. Separation and purification was achieved by flash column chromatography using DCM:petrol (1:1). Two compounds were isolated as pale yellow solids.

Compound (5)

$^1$H and $^{13}$C NMRs showed expected signals.

The following transitions and phases were observed by optical. microscopy using crossed polarisers: K-55-I Compound (6)

$^1$H and $^{13}$C NMRs showed expected signals.

This compound was used as an intermediate in the following reactions.

5.47 mmol), triethylamine (20 ml), Pd(PPh$_3$)$_2$Cl$_2$ (catalytic) and copper (1) iodide (catalytic) in THF (30 ml) under an atmosphere of nitrogen over a period of 2 hours at 40° C. After 16 h, the solution was allowed to cool to room temperature. The solution was poured in to dichloromethane and washed with water. The DCM layer was removed, dried over sodium sulphate and evaporated to dryness to leave a residual black solid. Purification was achieved by flash column chromatography using DCM:petrol (1:1). On evaporation of the appropriate fractions a yellow solid (0.5 g) was isolated.

$^1$H and $^{13}$C NMRs showed expected signals.

The following transitions and phases were observed by optical microscopy using crossed polarisers:

K-64-I

EXAMPLE 3

Compound (7) was prepared as described below

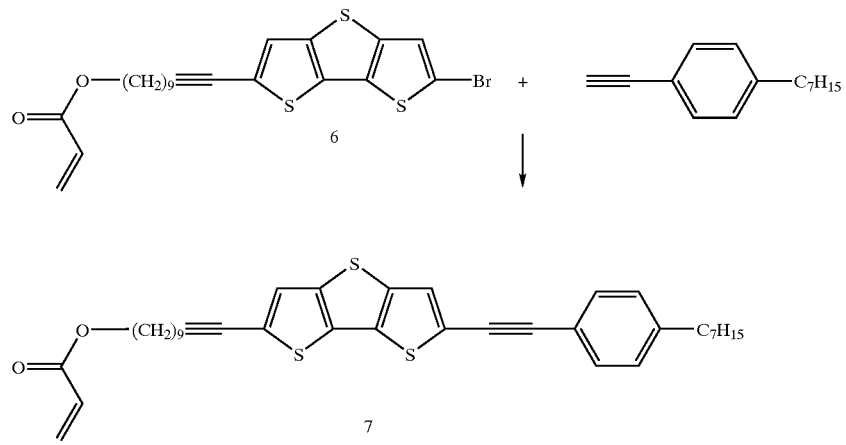

4-Heptylphenylacetylene (1.1 g, 5.47 mmol) in THF was added dropwise to a solution of DTT compound (6) (2.71 g,

EXAMPLE 4

Compound (8) was prepared as described below

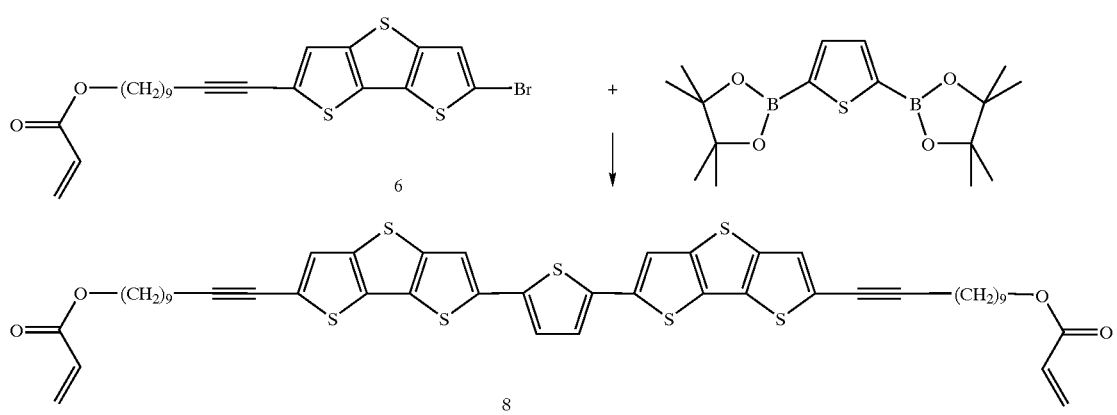

Thiophene bisboronate pinacol ester (0.57 g, 1.7 mmol) in THF was added dropwise to a solution of DTT compound (6) (1.68 g, 3.4 mmol) in toluene (30 ml), ethanol (30 ml), Pd(PPh$_3$)$_2$Cl$_2$ (catalytic) and sodium carbonate (0.72 g, 6.8 mmol) in water (20 ml) under an atmosphere of nitrogen over a 16 hours at reflux. The solution was allowed to cool to room temperature. The solution was poured in to dichloromethane and washed with water. The DCM layer was removed, dried over sodium sulphate and evaporated to dryness to leave a residual black solid. Purification was achieved by flash column chromatography using DCM-:petrol (1:1). On evaporation of the appropriate fractions an orange solid (0.34 g) was isolated.

$^1$H and $^{13}$C NMRs showed expected signals.

The following transitions and phases were observed by optical microscopy using crossed polarisers:
K-66-SB-71-SA-200-polymerises

EXAMPLE 5

Compound (10) was prepared as described below

DTT-bis acetylene compound (9) (0.9 g, 3.69 mmol) in THF was added dropwise to a solution of DTT compound (6) (3.65 g, 7.38 mmol), triethylamine (20 ml), Pd(PPh$_3$)$_2$Cl$_2$ (catalytic) and copper (1) iodide (catalytic) in THF (30 ml) under an atmosphere of nitrogen over a period of 2 hours at 40° C. After 16 h, the solution was allowed to cool to room temperature. The solution was poured in to dichloromethane and washed with water. The DCM layer was removed, dried over sodium sulphate and evaporated to dryness to leave a residual black solid. Purification was achieved by flash column chromatography using DCM:petrol (4:1). On evaporation of the appropriate fractions a red solid (0.32 g) was isolated.

$^1$H and $^{13}$C NMRs showed expected signals.

The following transitions and phases were observed by optical microscopy using crossed polarisers:
K-112-S-212-decomposed

What is claimed is:
1. A compound of formula I

P—Sp—T—R     I wherein

P is a polymerizable or reactive group,

Sp is a spacer group or a single bond,

R is H, halogen, CN, NO$_2$, an aliphatic, alicyclic or aromatic group with up to 40 C atoms that optionally comprises at least one hetero atom and/or at least one fused ring, or is P—Sp—, and T is a group comprising at least two fused thiophene rings, with the proviso that P is not trialkylsil.

2. A compound according to claim 1, wherein T is of formula II

—Z$^1$—(A$^1$—Z$^2$)$_m$—(T$^1$—Z$^3$)$_n$—(A$^2$—Z$^4$)$_o$—     II wherein

A$^1$ and A$^2$ are each independently an aromatic, heteroaromatic, alicyclic or heterocyclic group with up to 18 C atoms which is unsubstituted, mono- or polysubstituted with R$^1$, and A$^1$ may also denote T$^1$, Z$^1$ to Z$^4$ are each independently —O—, —S—, —CO—, —COO—, —OCO—, —O—COO—, —CO—NR$^0$—, —NR$^0$—CO—, —OCH$_2$—, —CH$_2$O—, —SCH$_2$—, —CH$_2$S—, —CF$_2$O—, —OCF$_2$—, —CF$_2$S—, —SCF$_2$—, —CH$_2$CH$_2$—, —CF$_2$CH$_2$—, —CH$_2$CF$_2$—, —CF$_2$CF$_2$—, —CH=N—, —N=CH—, —N=N—, —CH=CR$^0$—, —CX$^1$=CX$^2$—, —C≡C—, —CH=CH—COO—, —OCO—CH=CH— or a single bond, X$^1$ and X$^2$ are each independently H, F, Cl or CN, T$^1$ is 2, 3, 4, 5 or 6 fused thiophene rings which may also be substituted by R$^1$, R$^1$ is H, halogen, CN, NO$_2$, an aromatic or heteroaromatic group, P—Sp, or straight chain, branched or cyclic alkyl with up to 20 C-atoms, which may be unsubstituted, mono- or poly-substituted by F, Cl, Br, I or CN, in which at least one non-adjacent CH$_2$ group is optionally independently replaced by —O—, —S—, —NH—, —NR$^0$—, —SiR$^0$R$^{00}$—, —CO—, —COO—, —OCO—, —OCO—O—, —S—CO—, —CO—S—, —CH=CH— or —C≡C— in such a manner that O and/or S atoms are not linked directly to one another, R$^0$ and R$^{00}$ are independently of each other H or alkyl with 1 to 12 C-atoms, m and o are independently of each other 0, 1, 2 or 3, and n is 1, 2 or 3.

3. A compound according to claim 2, wherein $T^1$ is

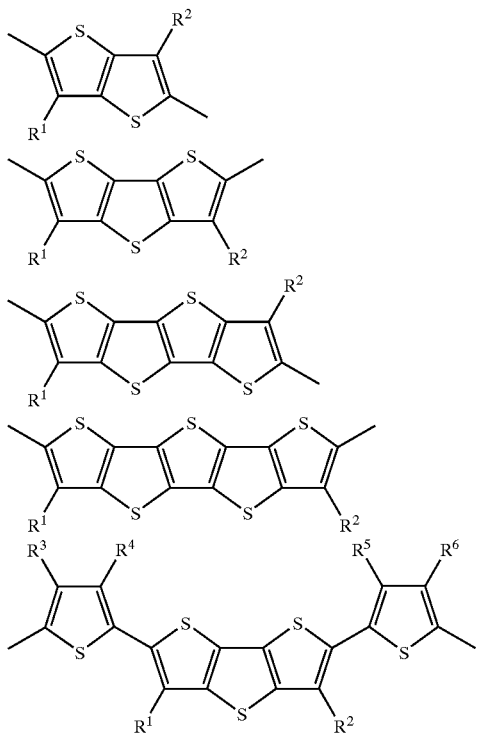

wherein $R^1$, $R^2$, $R^3$, $R^4$, $R^5$ and $R^6$ each independently have one of the meanings of $R^1$ in formula II.

4. A compound according to claim 2, wherein $A^1$ and $A^2$ are 1,4-phenylene; 1,4-cyclohexa-1,3-diene; 1,4-cyclohexenylene, in which at least one CH group is optionally replaced by N and one or two non-adjacent $CH_2$ groups are optionally replaced by O and/or S; thiophene-2,5-diyl, thienothieophene-2,5-diyl; dithienothiophene-2,6-diyl; furan-2,5-diyl; 1,4-bicyclo-(2,2,2)-octylene; naphthalene-2,6-diyl; or indane-2,5-diyl; each being unsubstituted, mono- or polysubstituted by L, with L being halogen, CN, SCN, $NO_2$, $SF_5$ or an alkyl, alkoxy, alkylcarbonyl or alkoxycarbonyl group with 1 to 4 C atoms, in which at least one H atom is optionally replaced by F or Cl.

5. A compound according to claim 2, wherein R and $R^1$ to $R^6$ are H, F, Cl, CN, $NO_2$, an aromatic or heteroaromatic group, P—Sp or straight chain, branched or cyclic alkyl with 1 to 20 C-atoms, which is unsubstituted, mono- or polysubstituted by F, Cl, Br, I or CN, at least one non-adjacent $CH_2$ groups optionally being independently replaced, by —O—, —S—, —NH—, —$NR^0$—, —$SiR^0R^{00}$—, —CO—, —COO—, —OCO—, —OCO—O—, —S—CO—, —CO—S—, —CH=CH— or —C≡C— in such a manner that O and/or S atoms are not linked directly to one another.

6. A compound according to claim 1, wherein P is $CH_2=CW^1—COO—$, $W^2HC\underset{O}{\overset{}{—}}CH—$, $W^2\underset{(CH_2)_k—O—}{\overset{O}{—}}$, $CH_2=CW^2—(O)_{k1}—$, $CH_3—CH=CH—O—$, $HO—CW^2W^3—$, $HS—CW^2W^3—$, $HW^2N—$, $HO—CW^2W^3—NH—$, $CH_2=CW^1—CO—NH—$, $CH_2=CH—(COO)_{k1}—Phe—(O)_{k2}—$, Phe—CH=CH—, HOOC—, OCN— or $W^4W^5W^6Si—$, $W^1$ is H, Cl, CN, or phenyl, $W^2$ and $W^3$ are each independently H or alkyl with 1 to 5 C-atoms, $W^4$, $W^5$ and $W^6$ are each independently Cl, oxaalkyl or oxacarbonylalkyl with 1 to 5 C-atoms, Phe is 1,4-phenylene and $k_1$ and $k_2$ are each independently 0 or 1.

7. A compound according to claim 2, of the formulae

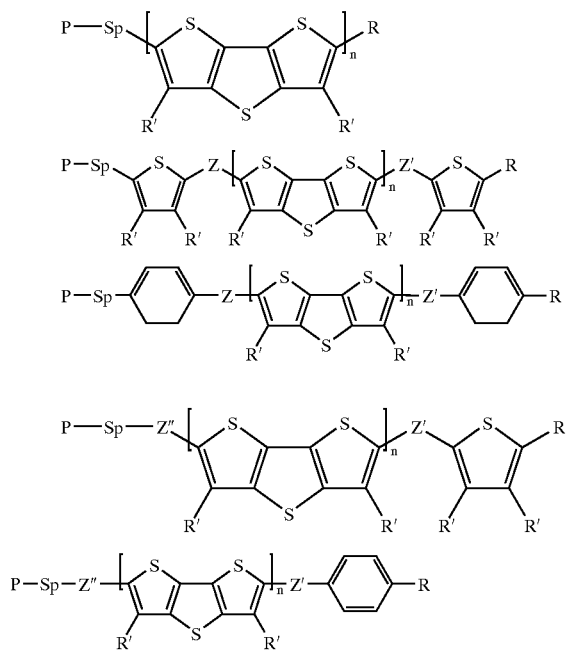

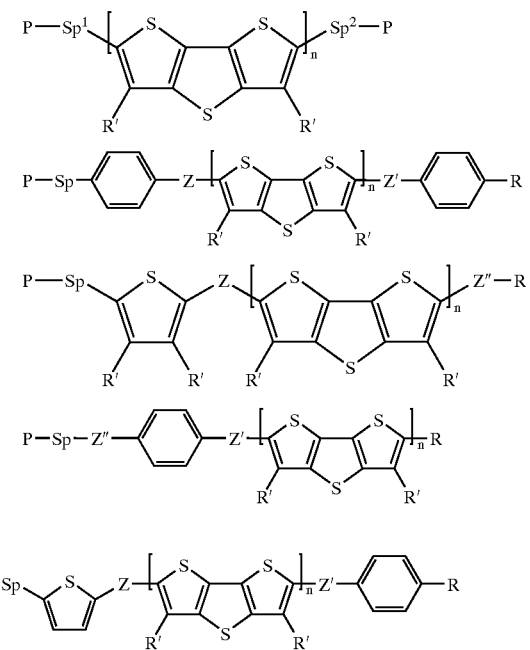

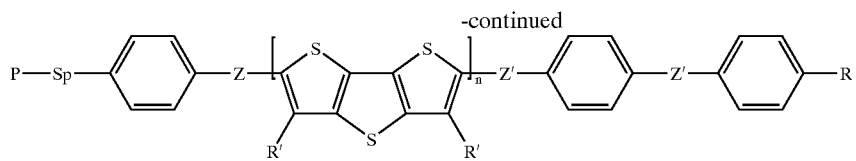

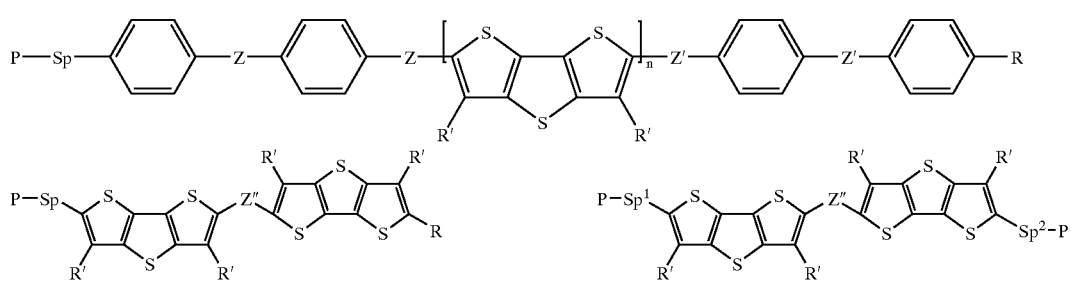

wherein P, $Sp^1$ and $Sp^2$ are different and are each independently groups as defined for Sp, Z and Z' is —CH=CH—, —CH=CF—, —CF=CH—, CH=CCl—, —CCl=CH—, —CF=CF—, —CCl=CCl—, —C≡C— or a single bond, Z" is —CH=CH—, —CH=CF—, —CF=CH—, CH=CCl—, —CCl=CH—, —CF=CF—, —CCl=CCl— or —C≡C—, R' is each independently one of the meanings of $R^1$.

8. A compound according to claim 1, which is mesogenic or liquid crystalline.

9. A reactive liquid crystal mixture comprising at least one compound according to claim 1 and optionally one or more further reactive compounds, wherein at least one of said compounds is mesogenic or liquid crystalline.

10. A reactive liquid crystal mixture comprising at least one compound according to claim 2 and optionally one or more further reactive compounds, wherein at least one of said compounds is mesogenic or liquid crystalline.

11. An anisotropic polymer film with charge transport properties obtainable from a reactive liquid crystal mixture according to claim 9 that is aligned in liquid crystal phase into macroscopically uniform orientation and polymerized or crosslinked to fix the orientation.

12. A side chain liquid crystal polymer obtained by polymerization of at least one compound or polymerizable material according to claim 1, and/or optionally one or more additional mesogenic or non-mesogenic comonomers, by grafting at least one compound or a polymerizable material according to claim 1 to a polymer backbone.

13. A semiconductor or charge transport material in an optical, electrooptical or electronic device comprising a compound of claim 1.

14. A semiconductor or charge transport material in an optical, electrooptical or electronic device comprising a reactive mixture of claim 9.

15. A semiconductor or charge transport material in an optical, electrooptical or electronic device comprising a polymer according to claim 11.

16. A semiconductor or charge transport material in an optical, electrooptical or electronic device comprising a polymer according to claim 12.

17. A semiconductor or charge transport material according to claim 13, which is an integrated circuit, field effect transistor, thin film transistor in a flat panel display application, a Radio Frequency Identification tag, a semiconducting component in an organic light emitting diode application, an electroluminescent display device, a backlight, a photovoltaic or sensor device, an electrode material in a battery, a photoconductor electrophotographic recording device or security device.

18. A compound, according to claim 1, which is oxidatively or reductively doped to form a conducting ionic species.

19. A polymer according to claim 11, which is oxidatively or reductively doped to form a conducting ionic species.

20. A charge injection layer, planarizing layer, antistatic film, conducting substrate, pattern for electronic application or flat panel display, comprising a compound according to claim 1.

21. A charge injection layer, planarizing layer, antistatic film, conducting substrate, pattern for electronic application or flat panel display, comprising a polymer according to claim 11.

22. A compound according to claim 1, of the formula

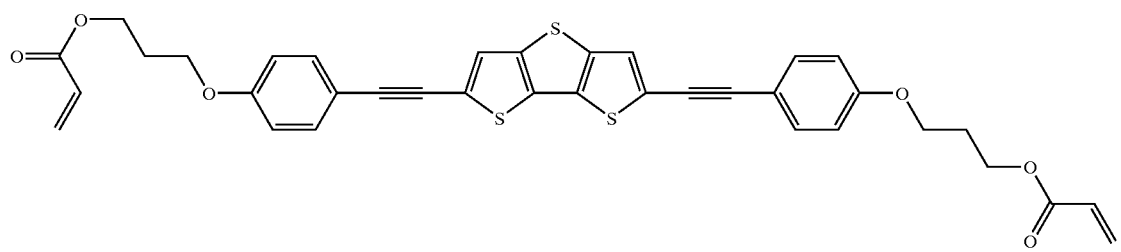

-continued

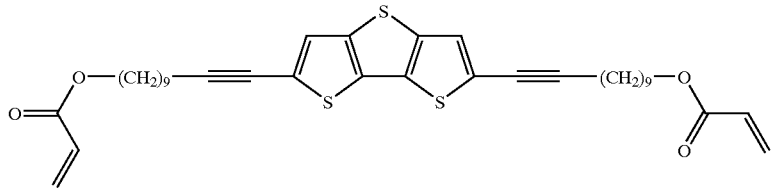

5

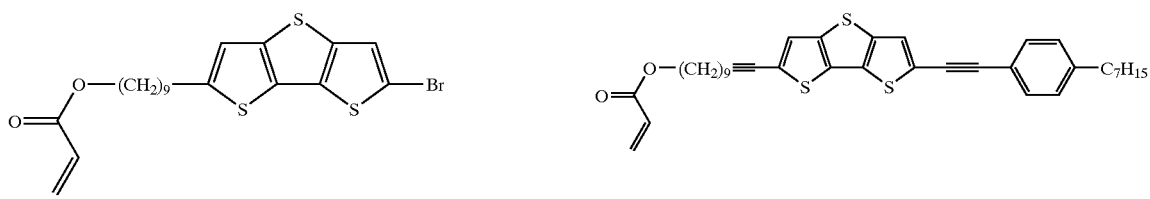

6

7

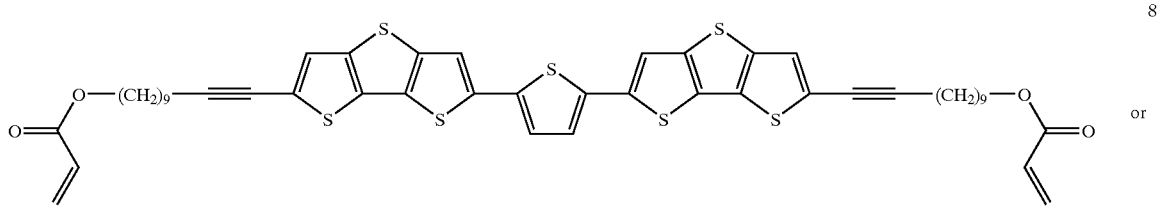

8

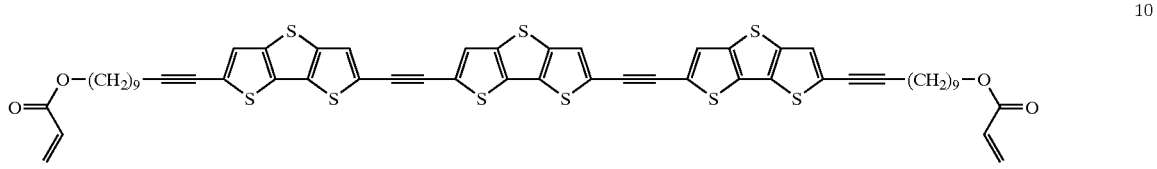

or

10

23. A compound according to claim 1, wherein R is H, halogen, CN, NO₂, an aliphatic group with up to 40 C atoms, 1,4-phenylene, 1,4-cyclohexa-1,3-diene; 1,4-cyclohexenylene, in which at least one CH group is optionally replaced by N and one or two non-adjacent CH₂ groups are optonally replaced by O and/or S; thiophene-2,5-diyl, thienothieophene-2,5-diyl; dithienothiophene-2,6-diyl; furan-2,5-diyl; 1,4-bicyclo-(2,2,2,)-octylene; naphthalene-2,6-diyl; or indane-2,5-diyl; each being unsubstituted, mono- or polysubstituted by L, with L being halogen, CN, SCN, NO₂, SF₅ or an alkyl, alkoxy, alkylcarbonyl or alkoxycarbonyl group with 1 to 4 C atoms, in which at least one H atom is optionally replaced by F or Cl.

24. A compound according to claim 2, wherein R¹ is H, halogen, CN, NO₂, an alphatic group with up to 40 C atoms, 1,4-phenylene, 1,4-cyclohexa-1,3-diene; 1,4-cyclohexenylene, in which at least one CH group is optionally replaced by N and one or two non-adjacent CH₂ groups are optonally replaced by O and/or S; thiophene-2,5-diyl, thienothieophene-2,5-diyl; dithienothiophene-2,6-diyl; furan-2,5-diyl; 1,4-bicyclo-(2,2,2)-octylene; naphthalene-2,6-diyl; or indane-2,5-diyl; each being unsubstituted, mono- or polysubstituted by L, with L being halogen, CN, SCN, NO₂, SF₅ or an alkyl, alkoxy, alkylcarbonyl or alkoxycarbonyl group with 1 to 4 C atoms, in which at least one H atom is optionally replaced by F or Cl.

* * * * *